United States Patent [19]

Bertling

[11] Patent Number: 4,950,599

[45] Date of Patent: Aug. 21, 1990

[54] METHOD FOR EXCHANGING HOMOLOGOUS DNA SEQUENCES IN A CELL USING POLYOMA ENCAPSULATED DNA FRAGMENTS

[76] Inventor: Wolf Bertling, 423 Whitehead Cir., Chapel Hill, N.C. 27514

[21] Appl. No.: 8,262

[22] Filed: Jan. 29, 1987

[51] Int. Cl.$^5$ .................... C12N 15/00; C12N 5/10; C12N 7/01

[52] U.S. Cl. .................... 435/172.3; 435/91; 435/235; 435/240.2; 435/948; 935/70; 935/71; 935/57; 935/32

[58] Field of Search .............. 435/172.3, 948, 91, 435/235, 69.1, 70.1, 235, 240.2; 935/32, 57, 70, 71

[56] References Cited

PUBLICATIONS

Bertling, W., *Bioscience Reports*, 7, No. 2, 107, (1987).
Smith, A. J. H. and Berg, P., *Cold Spring Harbor Symp. Quant. Biol.*, 49, 171, (1984).
Lin, F.-L. et al., *Proc. Natl. Acad. Sci.*, 82, 1391, (1985).
Thomas, K. R. and Capecchi, M. R., *Cell*, 51, 503, (1987).
Qasba and Aposhian, 1971 Proc. Natl. Acad. Sci., U.S.A., 68(10), 2345-2349.
Maniatis et al., 1982, *Molecular Cloning*, pp. 13-14.
Bethesda Research Laboratories Catalogue, 1988, pp. 220-221.
Pomerantz Betal, 1984, Prog. Cancer Res. Ther., 30:37-45.
Joyner, Al et al., 1984, Prog. Cancer Res. Ther., 30:89-96.
U. Goodenough, *Genetics*, 538-50, (3d Ed. 1984).
Radding, C. M., *Ann. Rev. Genet.*, 16, 405, (1982).
Rauth, S. et al., *Proc. Natl. Acad. Sci. U.S.A.*, 83, 5587, (1986).
Thomas, K. R. et al., *Cell*, 44, 419, (1986).
Smithies, O. et al., *Nature*, 317, 230, (1985).
Orr-Weaver, T. L. et al., *Proc. Natl. Acad. Sci. U.S.A.*, 78, 6354, (1981).
Slilaty, S. N., Berns, K. I., and Aposhian, H. V., *The Journal of Biol. Chem.*, 257, 6571, (1982).
Slilaty, S. N. and Aposhian, H. V., *Science*, 220, 725, (1983).

*Primary Examiner*—Robin L. Teskin
*Assistant Examiner*—Michelle S. Marks
*Attorney, Agent, or Firm*—Bell, Seltzer, Park & Gibson

[57] ABSTRACT

A method for altering a cell by exchanging a preselected cellular DNA sequence with an exogenous DNA sequence different from the cellular DNA sequence employs an exogenous DNA sequence encapsidated in a polyoma or polyoma-like capsid. The polyoma capsid is then contacted to the cell so that the exogenous DNA sequence is introduced within the cell and exchanges with the preselected cellular DNA sequence by homologous recombination.

A preferred article of manufacture comprises a polyoma capsid and a plurality of DNA sequences encapsulated within the polyoma capsid. The DNA sequences each comprise not more than an incomplete portion of a single preselected gene.

The exogenous DNA sequence may optionally be complexed to a DNA binding protein, such as a recA protein, prior to encapsulating the exogenous DNA sequence within a viral capsid, so that the uptake of the DNA sequence into the capsid is enhanced.

18 Claims, 1 Drawing Sheet

METHOD FOR EXCHANGING HOMOLOGOUS DNA SEQUENCES IN A CELL USING POLYOMA ENCAPSULATED DNA FRAGMENTS

FIELD OF THE INVENTION

This invention relates to recombinant DNA procedures generally, and particularly relates to procedures for the exchange of preselected DNA sequences in cells with exogenous, homologous DNA sequences.

BACKGROUND OF THE INVENTION

Homologous genetic recombination (sometimes called general recombination) is a naturally occuring process in many cells. While the actual mechanisms mediating this process are not firmly established, it involves the exchange of equivalent lengths of single stranded DNA between two interacting double stranded DNA segments. In the Holliday model of homologous recombination (named for Robin Holliday, who proposed the model in 1964) two similar, double stranded DNA segments (called duplexes) align with one another. After this, one single strand in each duplex breaks, and its free end invades the other duplex and ligates to the remaining end of the other broken strand. The resulting molecule is called a Holliday intermediate, and the location where strands cross over into opposite duplexes is known as a branch. In the final step of this process, the Holliday intermediate is cut in the region of the branch, and the cut ends are ligated to form two separate recombinant duplexes. Often these recombinant DNA molecules contain mismatched, or heterologous, base pairs: such molecules are called heteroduplex, or heterozygous, DNA molecules. See generally U. Goodenough, *Genetics*, 538–50 (3d Ed. 1984).

Homologous recombination is mediated by a protein called the recA protein In vitro, recA protein can induce a single stranded DNA fragment to invade a double stranded DNA segment and pair with a homologous region. The properties of recA protein, and the process of homologous recombination, are reviewed in Radding, C.M., *Ann. Rev. Genet.* 16, 405 (1982).

The possibility for the integration of exogenous DNA into eukaryotic cells by homologous recombination has been the subject of recent investigations by several groups. Rauth, S. et al., *Proc. Natl. Acad. Sci. USA* 83, 5587 (1986) examined the ability of circular, single-stranded DNA to participate in a homologous recombination event in mammalian cells by inserting a fragment of the neomycin resistance gene into a single-stranded vector, mixing the vector with a double-stranded deletion derivative of pSV2neo, and testing the mixture for recombination in human cells, monkey cells, and nuclear extracts obtained from human cells. Recombinant molecules containing wildtype neomycin resistance genes, apparently resulting from a correction of the deletion in the double-stranded pSV2neo deletion derivative, were recovered from all three systems.

Thomas, K.R. et al., *Cell* 44, 419 (1986) describe a homologous recombination event between a gene residing in a eukaryotic cell chromosome and an exogenous gene introduced into the cell by microinjection. The chromosomal gene was a defective neomycin resistance gene which had been inserted into a plasmid, and the plasmid then inserted into the chromosome. The exogenous gene was similarly located in a plasmid.

Smithies, O. et al., *Nature* 317, 230 (1985) describe an elegant procedure in which a homologous recombination event was used to insert an exogenous plasmid into a predetermined location in a mammalian chromosome, with the exogenous plasmids being introduced into the cells by electroporation. This work built in part on the work of Orr-Weaver, T.L. et al., *Proc. Natl. Acad. Sci. USA* 78, 6354 (1981), who accomplished the integration of a plasmid into a yeast chromosome through a homologous recombination event.

Electroporation, noted in connection with the Smithies work cited above, is a process in which brief electric impulses of high field strength are used to reversably permeabilize cellular membranes. The pores created during this process permit the introduction of macromolecules such as DNA. A drawback of electroporation, however, is that it reduces the viability of treated cells by 5 to 10 percent. A decrease of this size is a significant disadvantage in such procedures, where the quantities being manipulated are small, and where the materials used can be very expensive.

Other methods which have been used to introduce DNA into cells for various purposes have their own limitations. The most frequently used method, the uptake of calcium phosphate/DNA co-precipitates, is of limited utility for non-adherent cells. Other chemical methods, such as DEAE dextran-mediated uptake, are not suitable for stable gene expression. Protoplast treatment with polyethyleneglycol, as with any chemical method, is inherently cytotoxic. Biological methods, such as protoplast fusion, the use of liposomes, or the use of viral and retroviral vectors are restricted either to certain cell types or by the presence of potentially harmful DNA in the newly transformed cell. There is, accordingly, a need for a simple, reliable procedure by which an exogenous DNA sequence can be introduced into a cell, for exchange with a homologous DNA sequence in the cell. While additional background materials are introduced and discussed below, applicant is unaware of any suggestion in any of these materials of the unique combination of features which comprise the invention disclosed herein.

SUMMARY OF THE INVENTION

Disclosed herein is a method for altering a cell by exchanging a preselected cellular DNA sequence harbored in the cell with an exogenous DNA sequence different from the cellular DNA sequence. In this method, the preselected cellular DNA sequence is located in an endogenous functional sequence, such as a gene, and has a complementary cellular DNA sequence paired thereto. The exogenous DNA sequence is selected to be not more than a single functional sequence, and is sufficiently homologous to the preselected cellular DNA sequence and of a length suitable to allow the exogenous DNA sequence to anneal to the complementary celluar DNA sequence. The method comprises contacting a viral capsid having at least one of the exogenous DNA sequences encapsulated therein to the cell, so that the exogenous DNA sequence is introduced within the cell, and the exchange of the preselected cellular DNA sequence with the exogenous DNA sequence is permitted to occur. This process takes advantage of the cell's existing machinery for mediating homologous recombination, and does not involve the introduction of an expression vector into the cell. Because the exogenous DNA sequence is different from the cellular DNA sequence, the result is the formation of recombinant, heteroduplex DNA in the cell.

Stated more specifically, the present invention is a method for altering an eukaryotic cell by exchanging a preselected cellular DNA sequence harbored in the cell with an exogenous DNA sequence different from the cellular DNA sequence, in which the preselected cellular DNA sequence is located in a gene which is a part of a chromosome in the cell, has a complementary cellular DNA sequence paired thereto, and comprises not more than an incomplete portion of the gene. In this more specific statement of the invention, the method comprises, first, selecting an exogenous DNA sequence of from about 100 to about 300 nucleotides in length, which is capable of serving as not more than an incomplete portion of the aforesaid gene, and which is sufficiently homologous to the preselected cellular DNA sequence to anneal to the complementary cellular DNA sequence. A plurality of these exogenous DNA sequences are then encapsulated within a polyoma capsid. The polyoma capsid is then contacted to the cell so that the exogenous DNA sequences are introduced within the cell, and the exchange of the cellular DNA sequence with one of the exogenous DNA sequences is permitted to occur. When the aforesaid gene codes for the production of protein, at least some of the daughter cells of the cells which contain the recombinant, heteroduplex DNA will produce proteins that have predetermined alterations in their peptide sequences, and the nature of the alterations will be determined by the exogenous DNA sequence selected for exchange with the preselected cellular DNA sequence.

Cells altered by the foregoing methods are also an aspect of the present invention, as are the encapsulated, exogenous DNA sequences themselves. These encapsulated DNA sequences may be described as an article of manufacture, useful for altering cells by DNA exchange procedures, which articles comprise at least one DNA sequence encapsulated within a viral capsid. The encapsulated DNA sequence comprises not more than a single preselected functional sequence, such as a gene, has a length suitable to permit the DNA sequence to exchange with a homologous DNA sequence in a cell, and has a length allowing it to fit into the capsid.

In the present invention, viral capsid means for encapsulating the exogenous DNA sequence are employed. Pioneering work on viral capsids has been done by H. Vasken Aposhian and his colleagues. Slilaty, S.N., Berns, K.I., and Aposhian, H.V., *The Journal of Biol. Chem.*, 257, 6571 (1982), report that empty polyoma capsids can encapsulate a variety of different DNA sequences, and generally suggest that their data may be important in developing a vehicle for transferring nucleic acids across the mammalian cell membrane. Slilaty, S.N. and Aposhian, H.V., *Science* 220, 725 (1983), report that empty polyoma virus capsids can be used to encapsulate a restriction fragment of polyoma virus DNA, and that the encapsulated fragment can induce an oncogenic transformation in cells susceptible to the polyoma virus. These authors comment that this system, as a gene transfer system, is more efficient than calcium phosphate coprecipitation, and potentially provides a capability for gene transfer studies in vivo. However, these authors also comment that the usefulness of the system is limited by the size of the gene that can be encapsulated (the present invention is not so limited), do not suggest the use of the system in homologous recombination procedures, and nowhere suggest the encapsulation of DNA sequences of the type which this disclosure teaches should be encapsulated to carry out a homologous recombination procedure.

Applicant also discloses, in a process for encapsulating at least one DNA sequence within a viral capsid, the improvement comprising complexing the DNA sequence to a DNA binding protein prior to encapsulating the DNA sequence within the viral capsid. This improvement enhances the uptake of the DNA sequence into the capsid. A corrolary to this development is an article of manufacture comprising a complex of an exogenous DNA sequence and a DNA binding protein encapsulated within a viral capsid.

The present invention provides a simple, reliable procedure for carrying out homologous recombination events in cells. Among numerous other applications, the invention is useful for introducing predetermined changes in the amino acid sequence of proteins produced by cells—in other words, for engineering proteins produced by cells. The present invention is useful for altering cells in culture, and should have application for altering cells in animals: for example, by injecting the viral capsids into the circulatory system of an animal species.

DETAILED DESCRIPTION OF THE INVENTION

Figure 1:
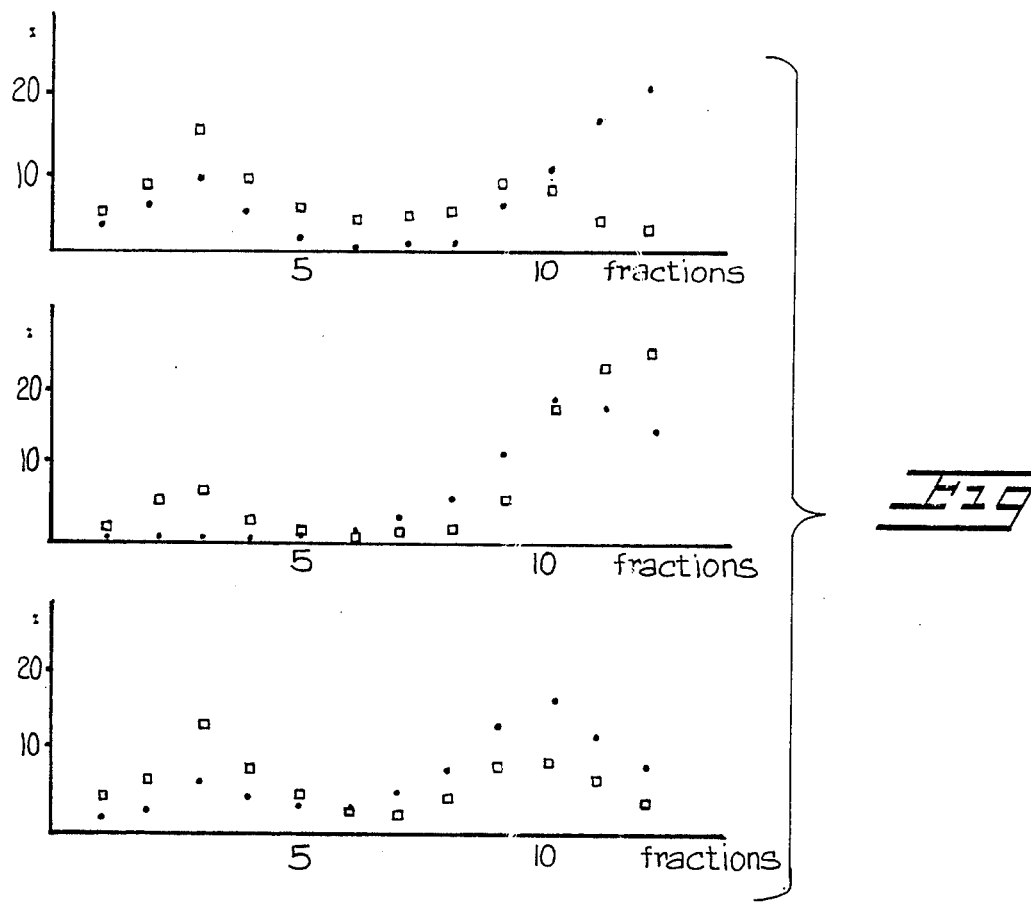
FIG. 1 shows cesium chloride/sucrose gradient centrifugation experiments verifying the encapsulation of DNA sequences comprising a fragment of the human HPRT gene in polyoma capsid.

Preselected cellular DNA sequences chosen for manipulation by the present invention are located in single endogenous functional sequences. The term "single functional sequence" is herein intended to encompass those smallest units of DNA which can be defined that still serve a specific function within a cell. Exemplary are genes, promoter sites, operators, and origins of replication. Excluded are operons, which are comprised of several such functional units. The term "endogenous" means originating within the cell, and the term "exogenous" means originating outside the cell. Such endogenous functional sequences are preferably single endogenous genes. Most preferably, the endogenous functional sequence is a gene which codes for the production of a protein. In addition, these functional sequences are preferably located on a chromosome of the cell chosen for manipulation, though they may also be located elsewhere in the cell, such as on viral DNA harbored within the cell.

The size of the preselected cellular DNA sequence, in addition to its location, is important to an understanding of the present invention. The cellular DNA sequence to be replaced should be of a length not greater than the endogenous functional sequence in which it is located, and is preferably not more than an incomplete portion of the endogenous functional sequence in which it is located.

The exogenous DNA sequence is also not more than a single functional sequence in length. The term "single functional sequence" has the same meaning here as explained in connection with the cellular DNA sequence above. As with the cellular DNA sequence, the exogenous DNA sequence is preferably not more than an incomplete portion of such a single functional sequence. The functional sequence is preferably a gene, and more preferably a gene which codes for the production of a protein. Most preferably, the functional sequence is a gene and codes for the production of a protein, and the exogenous DNA sequence codes for the production of a polypeptide which forms not more than an incomplete portion of the protein.

The exogenous DNA sequence can be obtained in accordance with procedures known in the art. See, e.g. Maniatis, T. et al., *Molecular Cloning: A Laboratory Manual* (Cold Spring Harbor Laboratory, Cold Spring Harbor, N.Y. 1982); Old, R.W. and Primrose, S.B., *Principles of Gene Manipulation* (Blackwell Scientific Publications 3d Ed. 1985). For purification of fragments, an agarose or polyacrylamid gel and elution by electroelution or diffusion is most appropriate. To reduce the volume in which fragments are dissolved, precipitation methods or minicolumns such as the NACS "PREPAC" minicolumn (BRL Instruction Manual 1985), with subsequent precipitation, are known.

An object of the present invention is to provide an exogenous DNA sequence which can exchange with the cellular DNA sequence by the cell-mediated process of homologous recombination to produce a recombinant, heteroduplex DNA within the cell. To achieve this result, the exogenous DNA sequence must be sufficiently homologous to the cellular DNA sequence, and of a length suitable, to allow the exogenous DNA sequence to anneal to the complementary cellular DNA sequence.

The degree of homology required between the exogenous DNA sequence and the cellular DNA sequence, and the limits on the lengths of exogenous DNA sequences which can feasibly be used, are interrelated and hence not amenable to definition by absolute limits. For example, where a cellular DNA sequence is comprised of a two adjacent regions, a suitable exogenous DNA sequence might be comprised of two identical regions having a third region interposed therebetween. While such an exogenous DNA sequence need not be highly homologous to the cellular DNA sequence, its identical regions could anneal to the complementary cellular DNA sequence, with the interposed region looping outward, and successfully participate in a homologous recombination event leading to the introduction of a new sequence (Note, however, that when such a new sequence is introduced, the present invention is preferably carried out with a single stranded exogenous DNA sequence having no complementary DNA sequence paired therewith.). In addition, it is known that heteroduplex DNA molecules containing deletions can be formed, and the exogenous DNA sequences used to produce such molecules would not, strictly speaking, be highly homologous to the cellular DNA sequences with which they exchange. Additional information on homology requirements for homologous recombination, obtained from studies in *E. coli*, is provided in Watt, V.M., *Proc. Natl. Acad. Sci. USA* 82, 4768 (1985).

Preferably, however, the exogenous DNA sequence will be at least about 95% homologous with the cellular DNA sequence. That is, at least about 95% of the nucleotides in these two sequences will match. As to length, the exogenous DNA sequences is preferably from about 50 to about 5,000 nucleotides in length, and more preferably from about 100 to about 300 nucleotides in length.

As used herein, the term "DNA sequence" refers to single-stranded DNA, and "DNA segment" refers to double-stranded DNA. Exogenous DNA sequences used in the present invention may be in the form of a single-stranded DNA sequence having no complementary DNA sequence paired therewith, or in the form of a single-stranded DNA sequence have a complementary DNA sequence paired therewith to form a double-stranded DNA segment. When the possibility of the presence of a complementary DNA sequence is not specifically excluded herein, both single and double stranded DNA are contemplated as useful and within the scope of the invention.

Where no complementary DNA is present, the exogenous DNA sequence preferably has DNA binding protein complexed thereto. When a double-stranded DNA segment is used, it is preferably prepared to have protruding ends. Such protruding ends are preferably modified to prevent the polymerization of the double-stranded segment with a like DNA segment (e.g., the polymerization of the DNA segments with one another). Any modification which prevents the ends from serving as substrates for DNA ligase is suitable. Such modification may, for example, be carried out by dephosphorylation or thiophosphorylation (replacement of an oxygen in the phosphate group with a sulfur) of the protruding ends, in accordance with known procedures.

The use of double stranded exogenous DNA segments having blunt ends is still another approach for practicing the present invention. Preferably, however, blunt ended DNA segments will be shorter segments which will more readily separate, or melt, once they are introduced within the cell.

Viral capsids used in carrying out the present invention should be obtainable in empty form devoid of their endogenous nucleic acids, capable of taking up exogenous DNA sequences, and bind to the cell to be altered. Preferred viral capsids for practicing the present invention are Polyoma capsids, which are produced from infected mouse embryo cultures. See Aposhian, H.V. et al., *J. Virol.* 15, 645 (1975); Crawford, L.V., *Virology* 18, 177 (1962); and Winocur, E., *Virology* 19, 158 (1963). Procedures for packaging exogenous DNA into such capsids are known. See Slilaty, Berns and Aposhian, *supra*. An advantage of the present invention is that, by using empty viral capsids, no DNA save for the exogenous DNA sequence discussed herein will be encapsulated therein and taken into the cell being treated.

As to other viruses which may provide empty viral capsids useful for practicing the present invention, larger viruses are expected to be capable of taking up more exogenous DNA, and to be capable of carrying more exogenous DNA into a cell. Therefore, larger viruses are generally contemplated as preferable for practicing the present invention. Further guidance on selecting viruses useful for practicing the present invention is provided by the work of Aposhian and others on the polyoma virus, as noted above. These researchers were initially led to investigate the polyoma virus because it was observed to be a small plaque forming virus. Therefore, other small plaque viruses may be useful for practicing the present invention. Depending on the application to which the present invention is applied, the virus selected for its viral capsids may be one with a wide host range, or may be a more specific virus. Finally, viruses which require the presence of an identifier sequence on the nucleic acid to be encapsulated therein are not contemplated as useful for practicing the present invention.

The cells to be altered by the present invention are preferably eukaryotic cells, more preferably animal cells, still more preferably vertebrate cells, and most preferably mammalian cells. The term "eukaryotic cells" includes cells from the protoctista, fungi, plantae, and animalia kingdoms. The term "animal cells" includes cells from, for example, the phyla coelenterata, ascheliminthes, annelida, arthropoda, echinodermata, and chordata. The term "vertebrate cells" includes, for example, cells from the classes chondrichthyes, osteichthyes, amphibia, reptilia, and mammalia. The term "mammalian cells" includes, for example, cells from the orders monotremata, marsupialia, insectivora, dermoptera, chiroptera, primates, edentata, pholidota, lagomorpha, rodentia, cetacea, carnivora, tubulidentata, proboscidea, hyracoidea, sirenia, perissodactyla, and artiodactyla. The exogenous DNA sequence is preferably of eukaryotic origin, more preferably of animal origin, still more preferably of vertebrate origin, and most preferably of mammalian origin. These terms encompass DNA originating from eukaryotic, animal, vertebrate, and mammalian cells, as explained in connection with the cells to be altered above, and also include viral DNA to which such cells may be susceptible, and which may at times be harbored in such cells.

In practicing the present invention, the exogenous DNA sequence preferably has a DNA binding protein complexed thereto. Exemplary DNA binding proteins include single strand DNA binding (ssb) protein, and, preferably, proteins which bind to single stranded DNA and promote homologous recombination events. Proteins which bind to single stranded DNA and promote homologous recombination events may be more particularly described as recA proteins. The term "recA protein" as used herein is to be construed broadly, to encompass proteins performing the same function regardless of source, including recA originating from *E. coli* and *B. subtilis*, and including the protein commonly designated "rec1" originating from Ustilago. RecA protein is commercially available (e.g. United States Biochemical Corp.) or can be isolated using the plasmid pLC 1842 (proteus gene cloned into the plasmid pLC 1842 in *E. coli* KM 1842) according to the procedure described in Cox, M.M. et al., i The J. Biol. Chem. 256, 4676 (1981). The functions of recA protein in promoting homolgous recombination events are described in detail in Radding, supra.

The present invention is carried out with at least one exogenous DNA sequence, or complex of a DNA sequence and a DNA binding protein, encapsulated within the viral capsid. Preferably, however, a plurality of such exogenous DNA sequences or complexes are encapsulated. More preferably a multiplicity (for example, about 100 or more) of such exogenous DNA sequences or complexes are encapsulated.

The following examples are provided to more fully illustrate the present invention:

EXAMPLE 1

Preparation of DNA Sequences

A 165 base pair DNA segment was obtained from an M 13 mp 18 bacteriophage (commercially available from Bethesda Research Laboratory (BRL)), which contained a 0.76 kilobase fragment of the human Hypoxanthine-Phosphoribosyl-Transferase (HPRT) gene (cDNA). The 165 base pair segment comprised the last 165 base pairs of exon number three of the HPRT gene, starting from the 5' end of the gene. The HPRT gene has previously been cloned and characterized by T. Friedmann and colleagues. See Jolly, D.L., et al., *Proc. Natl Acad. Sci. USA* 80, 477 (1983). The vector was codigested with XhoI (10 units/10 milligrams (mg) DNA) and Hinc II (10 units/10 mg DNA) for 1–2 hours at 37° C. in a buffer containing Tris/HCl pH 7.8 10 mM, $MgCl_2$ 10 millimolar (mM), mercaptoethanol 6 mM, NaCl 110 mM, and Bovine Serum Albumin (BSA) 0.2 mg/ml (milliliter). To ensure removal of extraneous exons so that good homology between the exogenous DNA sequence and the cellular DNA sequence would be obtained, the DNA digest was then further digested with a third enzyme, MboII. See generally Bethesda Research Laboratories Catalogue and Reference Guide 1986, and other similar companies. The result was the provision of a double stranded DNA segment having protruding ends.

The digest solution was loaded on a polyacrylamide gel, electrophoretically separated, the gel stained with ethidium bromide, and the 165 base pair band removed to obtain a purified fragment. The purified fragment was dissolved in PL buffer (Tris/HCl pH 7.5 10 mM; NaCl 10 mM; Ethylenediamine-tetraacetate (EDTA) 1 mM) and, for some of the DNA, the two strands of the double-stranded fragment were separated on a polyacrylamide gel according to the technique described in Maxam, A.M. and Gilbert, W., *Meth. Enzymol.* 65, 499 (1980). Single-stranded DNA sequences were isolated from the gel by the elution method, with the use of a low TE buffer (Tris/HCl pH 7.8 10 mM; EDTA 1 mM) and 0.1 molar NaCl preferred. A diffusion time of two 8 hour periods at 50° C. was used, with a change of buffer (10 milliliters/microgram) in between. The DNA sequences were concentrated with a BRL "NACS" "PREPAC" minicolumn (elution with 2 molar low TE buffer) and subsequent precipitation, and the DNA dissolved in the appropriate concentration of PL buffer.

Some of the single-stranded DNA sequences thus obtained were complexed with recA protein. To bind single-stranded DNA quantitatively to recA, 3.6 mg recA and 0.5 micrograms (ug) DNA was used in a complexation buffer (25 mM Tris/Acetate pH 7.5; 12 mM Magnesium Acetate; 1 mM Dithiothreitol; 1 mM Adenosinetriphosphate; 5 ul/ml Creatine phosphokinase; and 10 mM Creatine phosphate). After incubation in a waterbath (without shaking) for 1 hour at 37° C., the DNA was bound to the recA protein.

EXAMPLE 2

Encapsulation of DNA Sequences in Viral Capsids

The viral capsids used were empty polyoma capsids. Both single and double stranded DNA sequences from example 1, dissolved in the buffers (1×PL) in the appropriate concentrations (0.2–0.5 micrograms of DNA per 5 ug of viral capsids in 1×PL buffer) were added to the packaging mix to give the following solution:
DNA, viral capsid in PL buffer:
add 1 ul BSA (2 mg/40 microliters (ul)(BRL)) 10×PL-buffer q.s. to make end volume of 100 ul 1×PL buffer.
This solution was incubated for 10 minutes at 37° C., then, after adding 350 ul bidistilled water, was incubated at 37° C. for another 20 minutes, after which 40 ul of 10×PL buffer, 4 ul of BSA (2 mg/40 ul (BRL)) and water was added for a total volume of 500 ul. This solution was used to transform cells.

Cesium chloride/sucrose gradients were performed to verify the encapsulation of the DNA sequences, with the results of these gradients set forth in FIG. 1. The gradients were prepared by overlaying 0.3 ml CsCl (1.7 rho in $H_2O$) with 1.0 ml 20% sucrose, 1.6 ml 15% sucrose, and 2.0 ml 10% sucrose in a 4.8 ml centrifugation tube. All sucrose solutions were prepared by diluting a 25% sucrose solution that was 50 mM Tris/Hcl pH 7.8 with low TE buffer to the desired sucrose concentration.

The upper graph of FIG. 1 shows a gradient performed with single-stranded DNA fragments in a complex with recA protein; this binary complex was encapsulated by viral capsids. Encapsulated material sediments in a peak around fraction 3. $^{32}P$-labeled single-stranded DNA fragments (squares) as well as $^{125}I$-labeled recA protein (dots) can be detected both encapsulated in viral proteins (fractions 2–4) and not encapsulated (fractions 8–13).

The middle graph of FIG. 1 shows a gradient with assays containing either single-stranded DNA and viral capsids (squares) or recA protein and viral capsids (dots). recA protein that was not complexed with single-stranded DNA was not taken up into viral capsids. On the other hand, single-stranded DNA was taken up into viral capsids even if it was not complexed with recA protein.

The lower graph of FIG. 1 compares gradients of single-stranded DNA fragments that were complexed (squares) or were not complexed (dots) with recA protein prior to the encapsulation reaction. The encapsulation process was favored for DNA that was complexed to recA protein.

EXAMPLE 3

Transformation of Cells with Encapsulated DNA Sequences

Example 1 explains the preparation of a single-stranded DNA sequence which comprises a fragment of the human HPRT gene 165 nucleotides in length. This particular sequence was selected for the purpose of altering HPRT-Munich Lymphocytes. HPRT-Munich, which is characterized by Wilson, J.M. and Kelley, W.N., The J. Biol. Chem. 259, 27 (1984), is a mutant form of HPRT that was isolated from a patient with gout and greatly reduced enzyme activity. $1-2\times10^6$ HPRT-Munich cells (logarithmic growth) were centrifuged down (800–1000 rpm 10 minutes at room temperature in a Sorvall GLC 2B centrifuge). 0.5 ml 2×Dulbecco's Modified Eagle's Medium (DMEM),(according to Gibco) were added to the cells in a culture flask and the flask carefully shaken to resuspend the cells. The solution with the encapsulated DNA (0.5 ml) was added and, after gently shaking, incubated for 2 hours at 37° C. in $CO_2$ atmosphere. The cell suspension was gently shaken every 15 minutes. After 2 hours the cell suspension was diluted with 1×DMEM to a volume of 10 ml, and incubated at 37° C.

Figure 2:
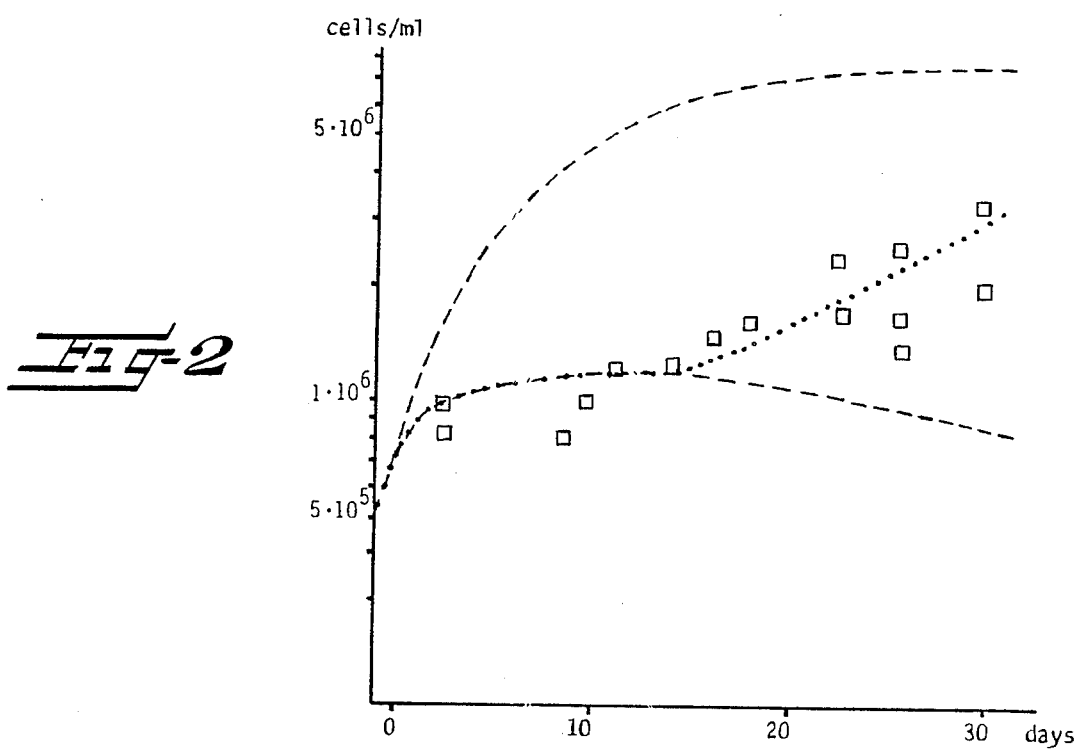
FIG. 2 shows the growth characteristics in HAT medium of HPRT-Munich lymphocytes treated (dotted curve and untreated (lower dashed curve) with polyoma-encapsidated fragments of the human HPRT gene.

Growth characteristics of treated and untreated cells over time are shown in FIG. 2. The upper dashed line represents the growth curve of hprt$^-$cells in normal growth medium. The lower dashed curve shows the reaction of these cells after adding Hypoxanthine-Aminopterine-Thymidine (HAT) medium at day zero. These 2 curves are averages of several experiments. Values obtained for individual measurements are not represented. The dotted curve shows the growth of hprt$^-$lymphocytes after adding at day zero HAT medium and the double-stranded 165 base pair DNA segments coding for a part of the exon III of the hprt gene, encapsulated in empty capsids of Polyoma virus, prepared as described in Examples 1 and 2 above. Values of individual cell counts of several experiments are indicated by squares.

These data show that cells survived treatment with the HAT selection medium only when they were treated with encapsulated DNA sequences, as described in this invention.

These examples have been provided for illustrative purposes only, and are not to be taken as restrictive of the present invention. The scope of the invention is defined by the following claims, with equivalents of the claims to be included therein.

That which is claimed is:

1. A method of altering, by homologous recombination, a preselected chromosomal DNA sequence encoding a protein in a polyoma-permissive cell, said method comprising the steps of:
   (a) providing a polyoma capsid having at least one single-stranded exogenous DNA sequence encapsulated therein,
   said exogenous DNA sequence consisting essentially of a DNA sequence sufficiently homologous to said preselected chromosomal DNA sequence and of a length suitable to anneal to the complement of said homologous DNA sequence, and
   (b) contacting said polyoma capsid to said polyoma-permissive cell so that said exogenous DNA sequence is introduced within said cell, anneals to the complement of said homologous DNA sequence, and exchanges with said chromosomal DNA sequence by homologous recombination.

2. A method according to claim 1, wherein said chromosomal DNA sequence comprises an incomplete portion of an endogenous structural gene in said cell, and wherein said exogenous DNA sequence is a fragment of said gene.

3. A method according to claim 1, wherein said polyoma-permissive cell is a mammalian cell.

4. A method according to claim 1, wherein said viral capsid has more than one of said exogenous DNA sequence encapsulated therein.

5. A method according to claim 1, wherein said exogenous DNA sequence is from about 50 to about 5,000 nucleotides in length.

6. A method according to claim 1, wherein said exogenous DNA sequence is single-stranded.

7. A method according to claim 6, wherein said exogenous DNA sequence has recA protein complexed thereto.

8. A method according to claim 1, wherein said exogenous DNA sequence is double-stranded, said double-stranded DNA sequence having protruding ends.

9. A method according to claim 8, wherein said protruding ends are modified to prevent the polymerization of said double-stranded DNA segment with a like DNA segment.

10. An article of manufacture useful for altering by homologous recombination a preselected chromosomal DNA sequence encoding a protein in a polyoma-permissive cell, said article comprising a polyoma viral capsid and at least one exogenous DNA sequence encapsulated within said polyoma viral capsid, said exogenous DNA sequence being sufficiently homologous to a strand of said preselected chromosomal DNA sequence to anneal to the complement thereof.

11. An article of manufacture as claimed in claim 10, wherein said exogenous DNA sequence consists of a fragment of said preselected chromosomal DNA sequence.

12. An article of manufacture as claimed in claim 10, wherein more than one of said exogenous DNA sequence is encapsulated within said polyoma viral capsid.

13. An article of manufacture as claimed in claim 10, wherein said DNA sequence is from about 50 to about 5,000 nucleotides in length.

14. An article of manufacture as claimed in claim 10, wherein said DNA sequence comprises a single-stranded DNA sequence.

15. An article of manufacture as claimed in claim 10, wherein said DNA sequence has RecA complexed thereto.

16. An article of manufacture as claimed in claim 10, wherein said DNA sequence is double-stranded, said double-stranded DNA sequence having protruding ends.

17. An article of manufacture as claimed in claim 16, wherein said protruding ends are modified to prevent the polymerization of said double-stranded DNA segment with a like DNA segment.

18. An article of manufacture useful for altering by homologous recombination a preselected chromosomal DNA sequence encoding a protein in a polyoma-permissive cell, said article comprising a polyoma capsid and at least one DNA sequence encapsulated within said polyoma capsid, said DNA sequence comprising not more than an incomplete portion of said chromosomal DNA sequence and having a length of from about 100 to about 300 nucleotides.

* * * * *